(12) United States Patent
Stewart, III

(10) Patent No.: US 7,815,584 B2
(45) Date of Patent: *Oct. 19, 2010

(54) ADJUSTABLE BACK SUPPORT DEVICE

(75) Inventor: Kenneth G. Stewart, III, Bradenton, FL (US)

(73) Assignee: The Idea People LLC, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/430,533

(22) Filed: Apr. 27, 2009

(65) Prior Publication Data

US 2010/0049109 A1    Feb. 25, 2010

Related U.S. Application Data

(63) Continuation of application No. 11/958,145, filed on Dec. 17, 2007, now abandoned, which is a continuation of application No. 11/004,121, filed on Dec. 6, 2004, now Pat. No. 7,309,304.

(51) Int. Cl.
*A61F 5/00* (2006.01)

(52) U.S. Cl. .......................................... 602/5; 482/148

(58) Field of Classification Search ................ 602/5, 602/19.5, 75.5; 482/148, 124, 104–108; 128/196.1; 2/255, 44, 311, 319; 102/3; 607/112, 607/108, 114; 126/104; 182/3

See application file for complete search history.

(56) References Cited

U.S. PATENT DOCUMENTS

| | | | |
|---|---|---|---|
| 4,189,182 A | 2/1980 | Rhoe | |
| 4,676,247 A | 6/1987 | Van Cleve | |
| 4,702,235 A | 10/1987 | Hong | |
| 4,837,859 A | 6/1989 | Hamberg | |
| 5,062,414 A | 11/1991 | Grim | |
| 5,146,625 A | 9/1992 | Steele et al. | |
| 5,179,942 A * | 1/1993 | Drulias et al. | 128/101.1 |
| 5,297,293 A | 3/1994 | Obujen | |
| 5,305,471 A | 4/1994 | Steele et al. | |
| 5,314,455 A | 5/1994 | Johnson, Jr. et al. | |
| 5,410,755 A | 5/1995 | Obujen | |
| 5,547,251 A | 8/1996 | Axelson | |
| 5,551,085 A | 9/1996 | Leighton | |
| 5,665,057 A * | 9/1997 | Murphy | 602/19 |
| 5,776,087 A | 7/1998 | Nelson et al. | |
| 5,797,143 A | 8/1998 | Buxton | |
| 5,928,275 A | 7/1999 | Yates et al. | |
| 5,948,013 A | 9/1999 | Swezey et al. | |
| 5,984,951 A | 11/1999 | Weiss et al. | |
| 6,588,020 B1 | 7/2003 | Stewart, III et al. | |
| 7,309,304 B2 * | 12/2007 | Stewart et al. | 482/124 |
| 2003/0195092 A1 | 10/2003 | Basting | |

* cited by examiner

*Primary Examiner*—Lori Baker
(74) *Attorney, Agent, or Firm*—Barnes & Thornburg LLP

(57) ABSTRACT

An adjustable device is described for applying pressure to an area of a person while substantially eliminating pressure from a prescribed area. The device includes a panel, a first elastic belt, a second elastic belt, a first elastic strap, and a second elastic strap. These elements are connected to one another such that the panel is flanked on one side by the first panel and the first elastic belt and, on the other side, by the second panel and the second belt. Alternate embodiments include several panels disposed side-by-side or on top of one another.

20 Claims, 5 Drawing Sheets

ADJUSTABLE BACK SUPPORT DEVICE

CROSS-REFERENCE TO RELATED APPLICATIONS

This application is a Continuation of U.S. patent application Ser. No. 11/958,145 filed on Dec. 17, 2007, now abandoned which is a Continuation of U.S. patent application Ser. No. 11/004,121, entitled "Adjustable Back Support Device," filed on Dec. 6, 2004, which is issued as U.S. Pat. No. 7,309,304 on Dec. 18, 2007, the contents of which are incorporated herein by reference.

BACKGROUND OF THE INVENTION

1. Field of the Invention

The invention relates to an adjustable body support device which applies supportive pressure to desired areas of a person's body in a manner which protects a prescribed area of the body from pressure due to contact with other objects.

More particularly, the invention relates to an adjustable back support device which is portable and can be used basically anywhere, in any setting as needed to provide support for a person's back while avoiding the application of pressure or contact in a sensitive area such as where there is an injury or surgery has been performed. The device is useful for persons recovering from back surgery or those with a back injury.

2. Description of the Related Technology

The present disclosure relates to applicants' U.S. Pat. No. 6,588,020 issued Jul. 8, 2003. The '020 patent is directed to a portable back support device for applying pressure to an area of a person's back while substantially eliminating pressure from a prescribed area of the back. A plurality of panels all connected to form a cover shaped to be placed on the back of a human torso are disclosed.

The '020 patent references U.S. Pat. Nos. 5,547,251, 5,146,625 and 5,062,414 in the description of related technology.

SUMMARY OF THE INVENTION

The invention is directed to a portable support device for applying supportive pressure selectively such that a confined area is not subject to the supportive pressure of the other areas. The device also assists in reducing gravitational, or other, compression of the vertebrae in a person's spine.

Other objects, advantages and novel features of the present invention will become apparent from the following detailed description of the invention when considered in conjunction with the accompanying drawings.

DETAILED DESCRIPTION OF THE PREFERRED EMBODIMENT

Figure 1:
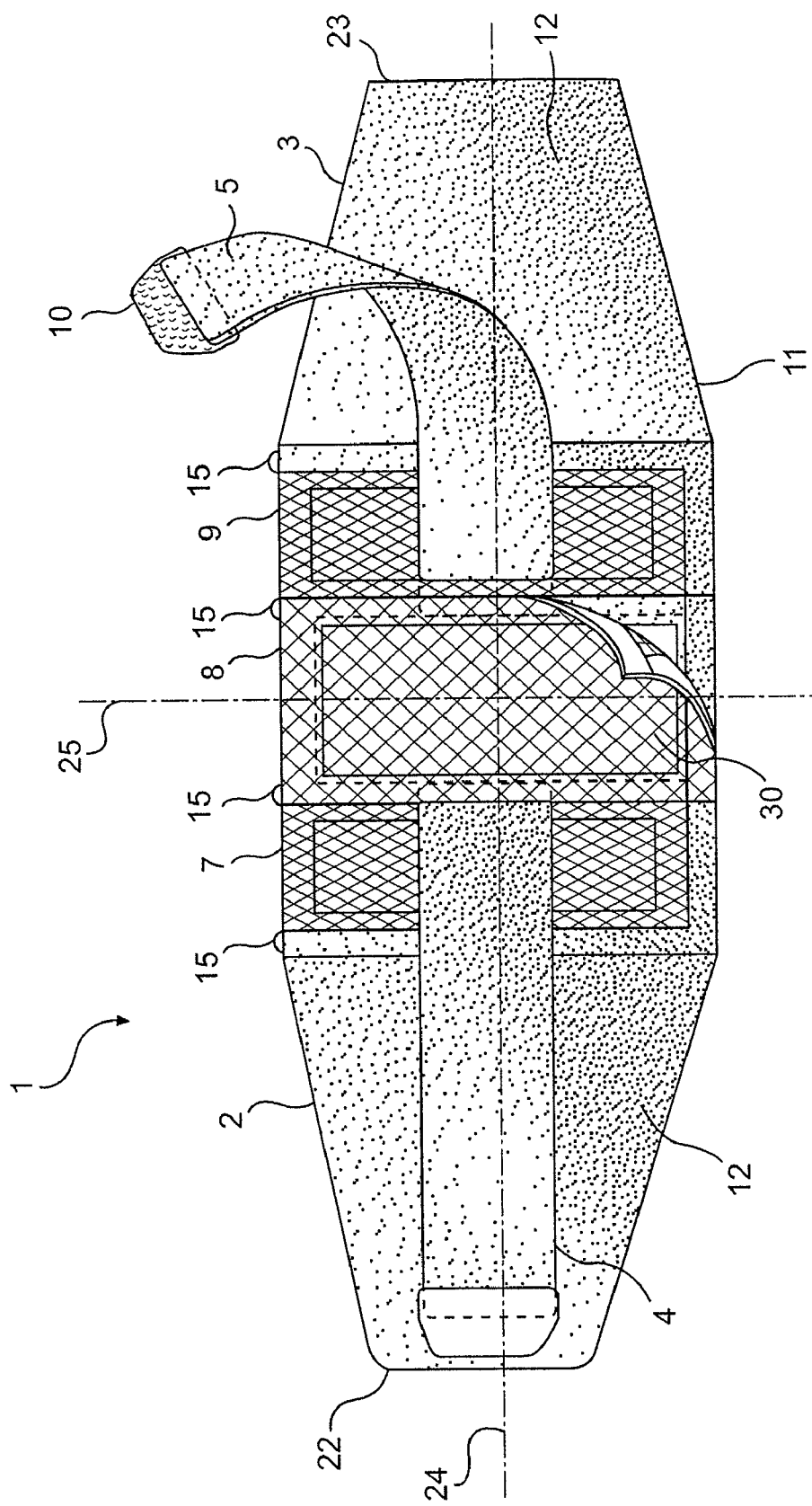
FIG. 1 shows a plan view of one embodiment according to the invention.

The preferred embodiment of the invention provides a belt-like support device which is designed to be strapped around the waist or other part of a person's body. The device is easily adjustable. In one embodiment it is adjustable by adding or removing panels to add length to the belt. As will become clear from the following description, the belt portions may be cut to shorten the belt length or longer belt portions may be used to lengthen the belt.

Panels are depicted in the drawing and they are of similar size and shape, however, it should be evident that panels of different lengths, widths and shapes are contemplated. In one preferred embodiment the device is generally shaped to fit the human torso and cover an area of the back between the shoulders and hips. The device includes structure which prevents pressure on a prescribed back area, such as an area which has been sutured or is otherwise recovering from injury or surgery. Contact with a sutured healing area can also cause irritation, lengthen healing time and prevent contact with air that promotes healing. The supportive device is also designed to relieve pressure on a person's vertebrae.

A person recovering from back surgery must be able to sit or lie in a back resting position without having pressure against the surgically recovering portion of the vertebrae. This is important for people recuperating at home and can be particularly important for persons who have returned to work and perform desk work such as secretaries, draftsmen, and the like whose seating arrangements would otherwise press against the back area where surgery has been performed. The supportive device or portable belt is adjustable to adjust the tension without removing or unfastening the belt. This is very helpful in that it permits frequent adjustment to maintain an acceptable level of comfort for the user.

The present invention provides a portable support device which may be used to provide acceptable support and comfort for a person while seated or lying down.

An optional feature is to provide a back support device that relieves compressive forces on the vertebrae.

A further additional feature is providing a sleep garment which protects a portion of a person's back (having stitches, etc.) from pressures and contact with different objects encountered when lying prone and turning while asleep.

Yet another aspect of the invention is that it allows mobility for persons recovering from, for example, spine surgery whereby they are able to use mass transit, their own personal automobile, etc. so as to be able to lean back against a seat or other support without pressure on, or contact with, portions of the person's back side.

The device also provides hot or cold pressure to assist in recovery from back surgery or to relieve back discomfort.

Figure 4:
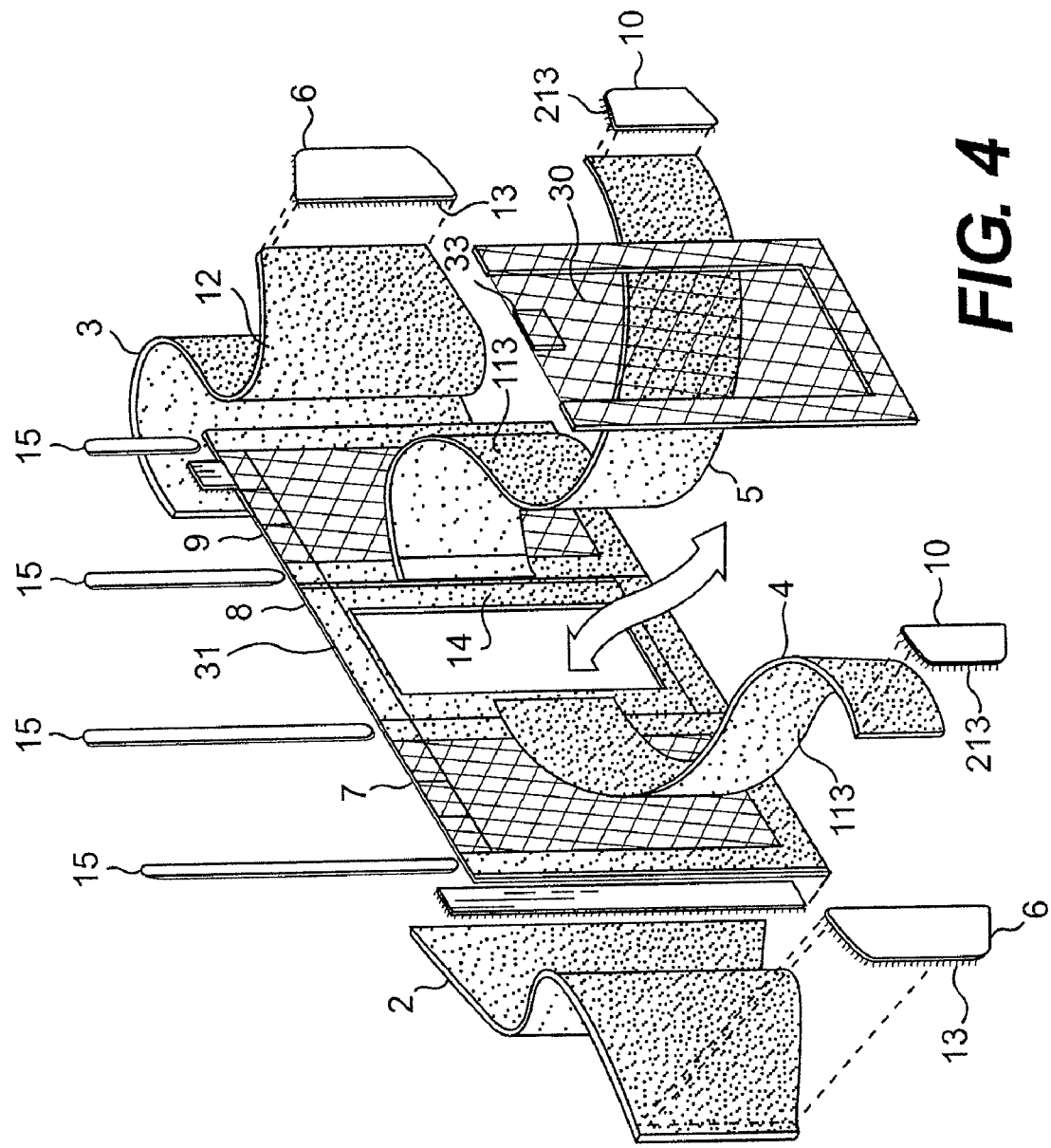
FIG. 4 is an exploded view of one embodiment of the invention.
Figure 5:
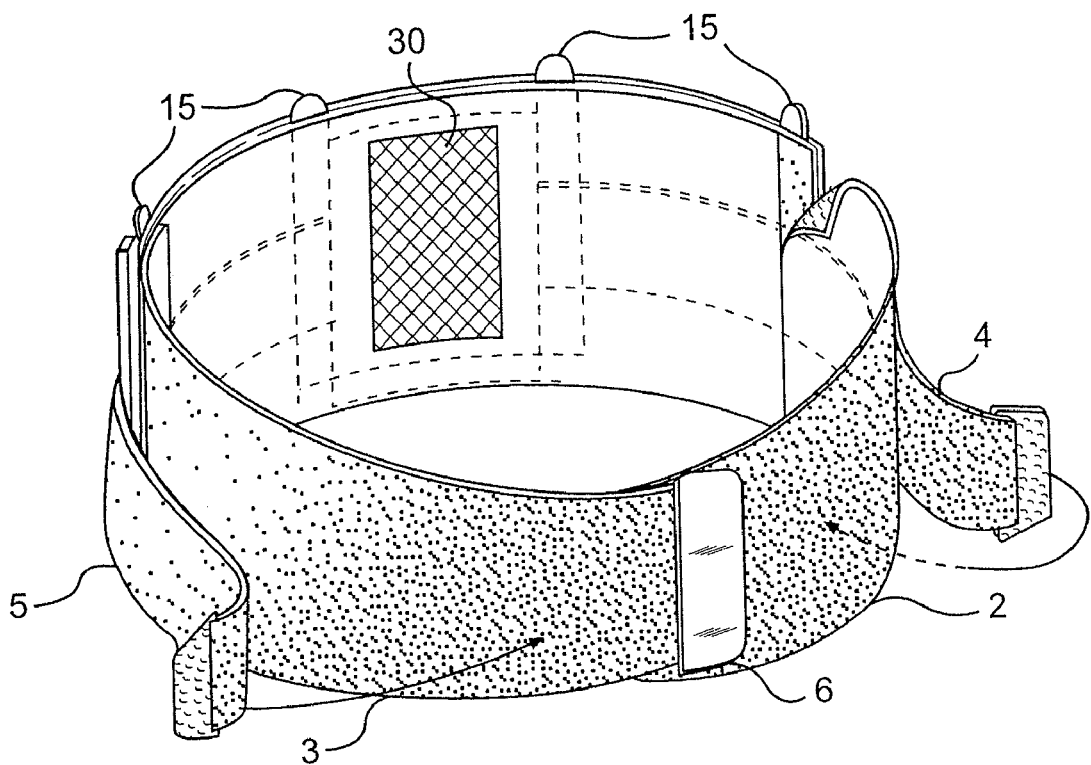
FIG. 5 shows a perspective view with the belt fastened.
Figure 6:
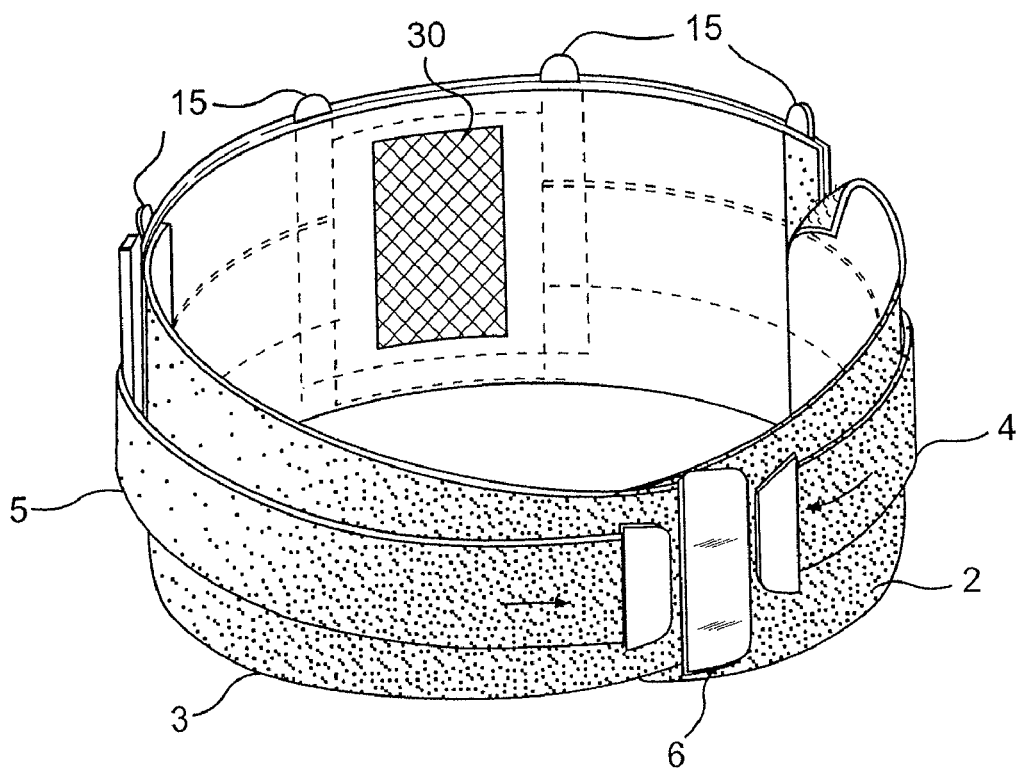
FIG. 6 shows a perspective view with the belt and straps fastened.
Figure 7:
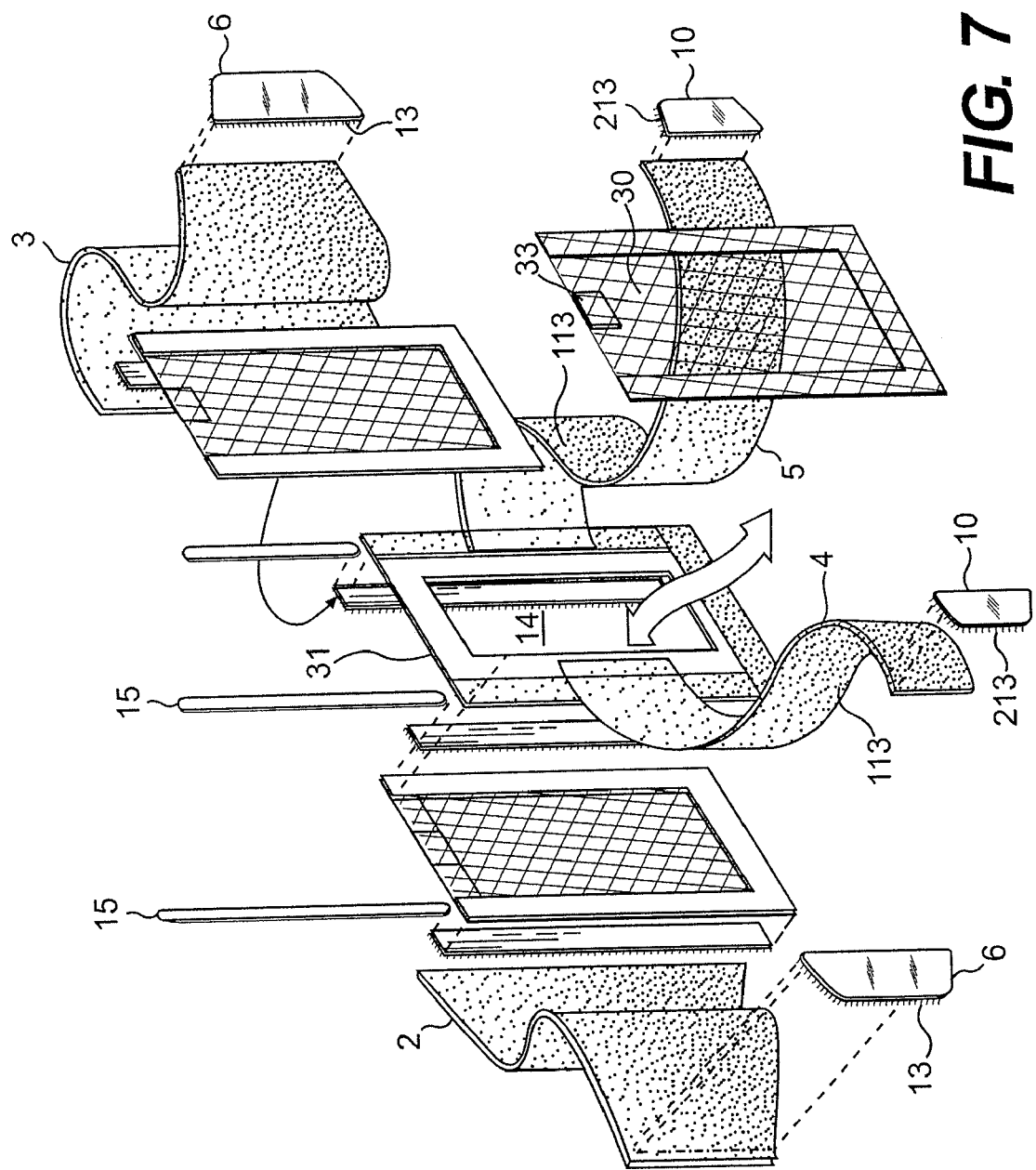
FIG. 7 is an exploded view of another embodiment of the invention.

As seen in FIG. 1 of the drawing there is shown an adjustable portable belt device 1 having three generally vertically extending panels 7, 8, 9. The adjustable portable belt device 1 has as elastic belt or belt portion 2 and an elastic belt or belt portion 3. Belts 2 and 3 may be portions of the same monolithic piece of elastic (as best seen in FIG. 1) or they may be separate pieces joined together (as best seen in FIGS. 4-7). In the embodiment of FIG. 4 panels 7, 8 , 9 are one piece with separate belts 2, 3 joined at the ends. In the embodiment of FIG. 7, elastic belt 2 is removably connected to panel 7, panel 7 is removably connected to panel 8 and panel 8 is removably connected to panel 9. In the present drawings, line 24 (see especially FIG. 1) depicts the belt device length direction and line 25 depicts the belt device width direction.

Panel 9 is removably connected to elastic belt 3. In one preferred embodiment each elastic belt portion 2, 3 is made out of a typically light-weight but strong elastic fabric 11 with loops 12 (in the drawings the loops are distributed over the surface of fabric 11) or other similar connectors on one side. Preferably the elastic fabric 11 is severable by a conventional household scissors or other similar cutting device so as to permit either, or both, belt portions 2 and 3 to be cut to a desired length. This will permit a user to be able to connect the desired number of panels to belts 2 and 3 then cut excess length from the belt end(s) so that each time the belt device 1 is used it will be of the correct relative length without too much excess length.

One end of belt portion 3 has a belt fastener 6 (FIG. 4). Fastener 6 is a section of fabric with hooks 13 or other similar type connectors on one side. Fastener 6 may be removable or permanently affixed to the belt 2, 3. As is evident from FIGS. 5 and 6 the belt may be wrapped around the desired body area and joined by fastener 6 which overlaps the end portion 23 of belt portion 3 and the end 22 of belt portion 2. One end of fastener 6 is attached to one end of belt 3 (as shown in FIGS. 4 and 5) and the opposite end of fastener 6 is attached to any portion of the belt 2 from the end 22 up to a panel (7, 8, or 9) so as to firmly attach the belt to the desired part of the person's body. When the belt device 1 is wrapped around the body the elastic belts 2, 3 are stretched as desired by the user to firmly secure the belt and apply a comfortable amount of tension on the belt 2, 3.

Belt device 1 has elastic straps 4, 5 for additionally adjusting the tension in belt device 1. Two elastic straps are shown, however, fewer or more such straps may be provided. One end of strap 5 may be fixed to the belt 3 at or near to its connection with panel 9 or as seen in FIG. 1 at or near panel 8. Elastic strap 5 can be stretched and then joined to underlying belt 3 thereby adding tension to the belt 3 and thus, to the belt device 1. Hook type fasteners 113 on one side of strap 5 are used to releasably join to the loops shown on the substantially on the entire surface of stretched belt 3 to maintain the belt 3 and belt device 1 in the position with the additionally applied tension from strap 5. Further belt device tension may be applied by stretching elastic strap 4 and then joining it to belt 2 thereby adding the additional tension in stretched strap 4 to belt 2. Thus, belt device 1 has tension from belts 2, 3 and additional tension from each of straps 4, 5. In an alternative embodiment straps 4 and 5 may comprise an elastic member with strap fastener 10 at one end as seen in FIGS. 4 and 5. Strap fastener 10 is like belt fastener 6 in that strap fastener 10 is a section of fabric with hooks 213 or other similar type connectors on one side. Fastener 10 may be removable or permanently affixed to the strap 4, 5. As is evident from FIG. 1 the strap fastener 10 may be joined to overlap one end of strap 5 and a portion of belt 3. One end of strap fastener 10 is attached at or near one end of belt 3 (as shown in FIG. 6) and the opposite end of strap fastener 10 is attached to any portion of the belt 3 so as to add tension to belt 3 and adjust belt device 1 as desired by the user. When using strap fasteners 10 the strap 4, 5 may or may not have loops 113 as desired.

It should be evident that while hooks are described on one surface and loops are described on a connecting surface, replacing the hooks with loops and the loops with hooks is also contemplated.

In a preferred embodiment straps 4 and 5, like belts 2 and 3 comprise an elastic sheet of fabric with hook or loop type fasteners affixed to one surface. In this manner a strap fastener 10 with hook 213 type fasteners on its underside (as seen in FIG. 7) can be attached to the top side (as seen in FIG. 1) of strap 5 and to the top side (as seen in FIG. 7) of belt 3. The same is true for strap 4 and belt 2.

Figure 2:
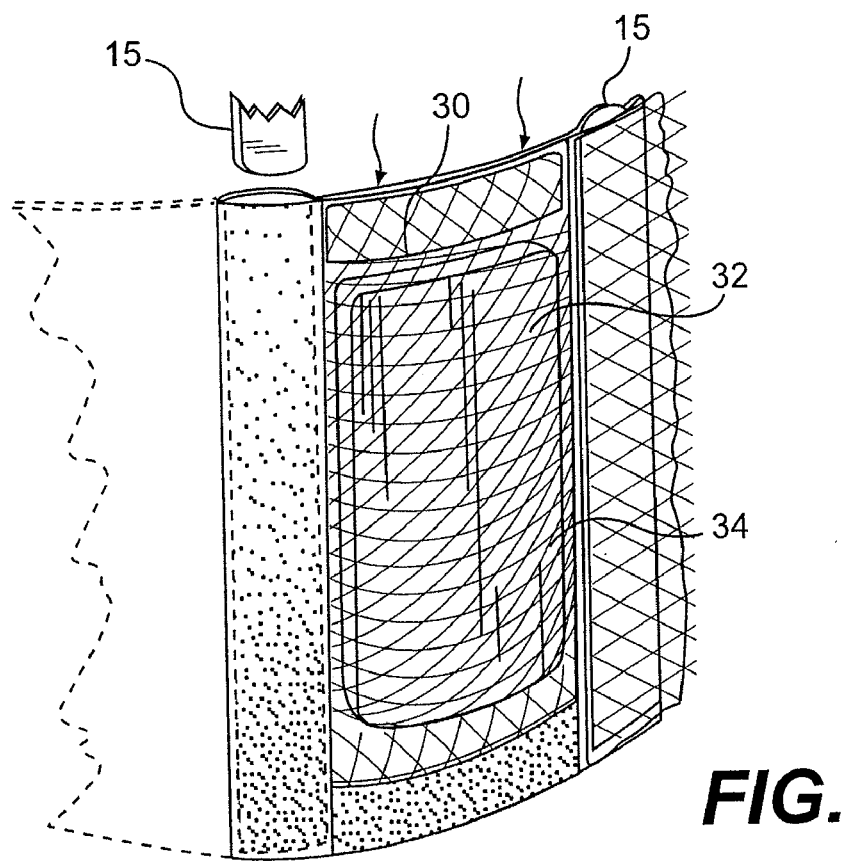
FIG. 2 shows a perspective view of one of the side panels of the invention.
Figure 3:
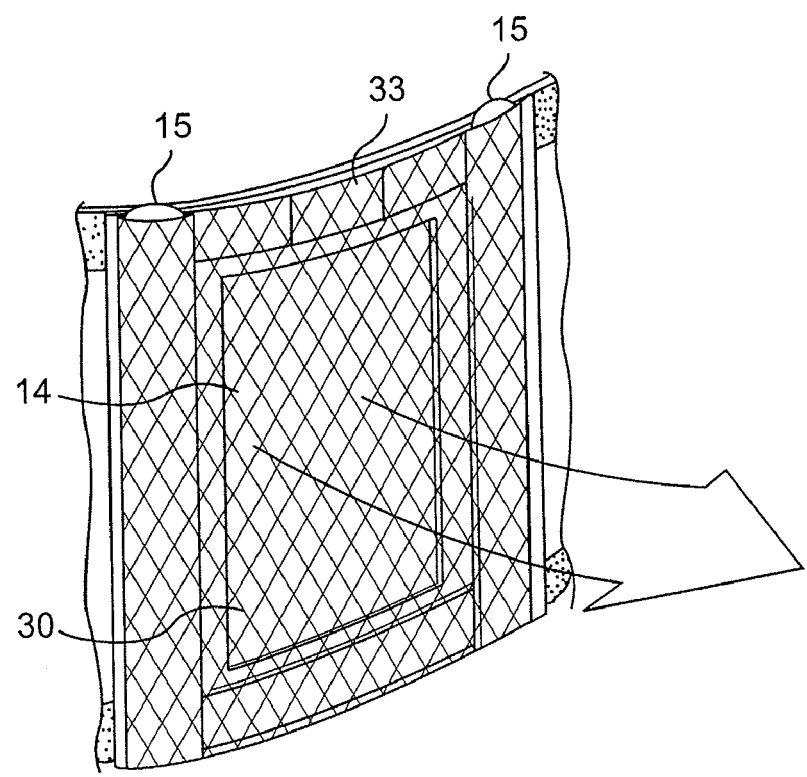
FIG. 3 shows a center panel.

Belt device 1 may include a plurality of panels 7, 8, 9. The number of panels and their arrangement may vary depending on the body area to be covered. The panels may be sewn together or releasably fastened together. In the construction shown in FIG. 1 the center panel 8 is generally air permeable so that air can promote healing of the affected area. The center panel 8 is made of one layer of thin mesh-like material 30 (FIG. 4) and a backing layer 31 with an opening 14. Opening 14 is large enough to surround a prescribed area of a person's anatomy to protect that area from pressure. In panel 8 a space is provided between the mesh-like material 30 and the backing layer 31 area for insertion and removal of an absorbent pad or dressing (not shown). The absorbent pad or dressing may reside between the mesh material 30 and the persons body by being hung on the mesh or provided on the person by being affixed (taped, etc.) to the person over the sutured incision. The mesh-like layer 30 loosely supports the absorbent pad or dressing. The backing layer 31 takes the tension on the belt device through the panel 8 so that the mesh-like material 30 can loosely fit over the panel 8, supports any pad or dressing, but will not press against the underlying prescribed area. In panels 7, 9 a space or pocket is provided between the mesh-like material 30 and the backing layer 31 for insertion and removal of a removable pack 32 (FIG. 2) of a hot or cold temperature retaining material for applying therapeutic thermal treatment. The panels 7 and 9 (FIG. 2) on either side of the center panel 8 (FIG. 3) have a thickness of ½ inch to three inches greater than the thickness of the center panel 8. All of the panels need not be of the same thickness and the thickness difference between panel 8 and, for example, panel 7 may reside in a pack 32 in the pocket of the panel 7. One edge of mesh-like material 30 may be releasably fixed by a pocket fastener 33 (as by a snap, button/hole, hook and loop, etc.) to panel 7, 8, 9 to permit insertion and removal of pack 32 into the pocket 34. It being understood that the other edges of the mesh-like material 30 are releasably or permanently fixed to the backing 31 along the periphery of the panels 7, 8, 9. For example, the mesh portion of center panel 8 may be removable fixed (as by hook and loop fasteners, buttons, snaps, etc.) to permit removal of the mesh to gain access to a bandage for cleaning of a wound and application of a clean bandage. The mesh portion may be fixed to panels 7 and 9 by being sewn to permanently fix the mesh to the panel.

The pockets 34 may be filled with an inflatable bag, with foam rubber as well as provided with a hot/cold gel pack 32. A suitable gel thermal pack that may be heated or cooled is described in U.S. Pat. No. 4,756,311. The panels 7, 8, 9 and pockets 34 may vary in shape, size and number.

When the belt device 1 is placed on a persons back such that the center panel 8 overlies the vertebrae the thickness of the adjacent panels 7, 9 prevents pressure on the center panel area when the person is seated or lying down. The pressure against the persons back is against the thicker side panels 7, 9, not the portion of their back covered by the thinner center panel 8. Thus the center panel 8 will cover an incision area while at the same time avoiding pressure being applied to the incision area. The difference in thickness between the center 8 and adjacent panels 7, 9 is great enough to permit a dressing to cover the sutured area without pressure.

As described above, when the adjustable belt device 1 is firmly affixed to a person's torso the panels 7, 8, 9 support the back or lumbar region so as to apply decompressive forces to the vertebrae. Stays or stiffeners 15 maintain the width of the belt and enhance this effect. Rigid stays 15 may be contoured to provide better support and comfort to the back or other body portion. As seen in for example FIG. 2, stay or stiffener 15 is held in place in a pocket of the belt device 1. Such pockets (shown in each of FIGS. 1-7) confine the contoured stiffener 15 to the desired location so as to advantageously apply pressure to the underlying body area. Stays or stiffeners 15 may be removed from the pockets to prevent support in an undesirable area. Removal of one or more stays 15 softens the feel of the belt device for the user and thus provides a greater range of comfort and support. The stays 15 may be retained in the pockets with or without a pocket fastener, like pocket fastener 33.

As best seen in FIG. 1, belt device 1 is shaped to accept tensional loading but not compression loading. Belts 2, 3 are elastic fabric which permits the panels to be stretched apart along length axis 24 so that the belt device is stretched taut (absorbs tensional loading) while the panel 8 has opening 14 to allow air circulation (FIG. 3) and prevent the application of pressure (does not permit compression) to that area of the person's anatomy.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. An adjustable back support device for applying pressure to an area of a person while substantially eliminating pressure from a prescribed area, comprising:
    a panel having an interior side, an exterior side, a top end, a bottom end, a first lateral end, and a second lateral end;
    a first elastic belt having an interior side, an exterior side, a top end, a bottom end, a third lateral end, and a fourth lateral end;
    a second elastic belt having an interior side, an exterior side, a top end, a bottom end, a fifth lateral end, and a sixth lateral end;
    a first elastic strap having an interior side, an exterior side, a top end, a bottom end, a seventh lateral end, and an eighth lateral end;
    a second elastic strap having an interior side, an exterior side, a top end, a bottom end, a ninth lateral end, and a tenth lateral end;
    wherein
    the third lateral end connects to the first lateral end;
    the fifth lateral end connects to the second lateral end;
    the seventh lateral end connects to the first lateral end;
    the ninth lateral end connects to the second lateral end;
    the fourth lateral end connects to the sixth lateral end;
    the interior side of the first elastic strap connects to the exterior side of the first elastic belt;
    the interior side of the second elastic strap connects to the exterior side of the second elastic belt;
    the interior sides of the panel, the first elastic belt, the second elastic belt, the first elastic strap, and the second elastic strap are aligned with one another;
    the exterior sides of the panel, the first elastic belt, the second elastic belt, the first elastic strap, and the second elastic strap are aligned with one another;
    the top ends of the panel, the first elastic belt, the second elastic belt, the first elastic strap, and the second elastic strap are aligned with one another; and
    the bottom ends of the panel, the first elastic belt, the second elastic belt, the first elastic strap, and the second elastic strap are aligned with one another.

2. The adjustable back support device of claim 1, wherein the eighth lateral end connects to the tenth lateral end.

3. The adjustable back support device of claim 1, wherein the panel comprises a plurality of panels connected to one another.

4. The adjustable back support device of claim 3, wherein the plurality of panels are connected laterally to one another to span a distance between the third lateral end and the fifth lateral end.

5. The adjustable back support device of claim 4, wherein the plurality of panels comprises three panels, a first panel forming a recessed covering for a prescribed area of the person's anatomy and being shaped to accept tensional loading but not compressional loading, and second and third panels, flanking the first panel, each having a thickness greater than the first panel, whereby the second and third panels are arranged for applying pressure to an area of a person's back while the first panel substantially eliminates pressure from a prescribed area of the back.

6. The adjustable back support device of claim 3, wherein the plurality of panels overlap one another, thereby forming a multilayer panel between the third lateral end and the fifth lateral end.

7. The adjustable back support device of claim 1, wherein the panel comprises an air permeable member.

8. The adjustable back support device of claim 7, wherein the panel comprises a mesh material.

9. The adjustable back support device of claim 1, further comprising:
    at least one pocket connected to at least one of the panel, the first elastic belt, or the second elastic belt; and
    at least one removable, rigid elongated contoured stay disposed within the at least one pocket.

10. The adjustable back support device of claim 9, wherein the at least one pocket comprises a plurality of pockets and the at least one removable, rigid elongated stay comprises a plurality of stays, each disposed within one of the plurality of pockets.

11. The adjustable back support device of claim 1, wherein:
    the third lateral end connects to the first lateral via hook and loop fasteners;
    the fifth lateral end connects to the second lateral end via hook and loop fasteners;
    the seventh lateral end connects to the first lateral end via hook and loop fasteners;
    the ninth lateral end connects to the second lateral end via hook and loop fasteners;
    the fourth lateral end connects to the sixth lateral end via hook and loop fasteners;
    the interior side of the first elastic strap connects to the exterior side of the first elastic belt via hook and loop fasteners; and
    the interior side of the second elastic strap connects to the exterior side of the second elastic belt via hook and loop fasteners.

12. The adjustable back support device of claim 1, further comprising:
    a first fastener attached to the fourth lateral end;
    a second fastener attached to the sixth lateral end;
    a third fastener attached to the eighth lateral end; and
    a fourth fastener attached to the attached to the tenth lateral end;
    wherein
    the first fastener connects with the second fastener, and
    the third fastener connects with the fourth fastener.

13. The adjustable back support device of claim 12, wherein the first, second, third and fourth fasteners comprise complimentary hook and loop fasteners.

14. The adjustable back support device of claim 6, wherein the multilayer panel forms a pocket into which at least one removable, thermal treatment pack may be placed.

15. The adjustable back support device of claim 14, wherein the removable, thermal treatment pack generates one of a hot or cold temperature.

16. The adjustable back support device of claim 1, wherein a width of the first and second elastic belts is greater than a width of the first and second elastic straps.

17. The adjustable back support device of claim 1, wherein at least one of the first elastic belt, the second elastic belt, first elastic strap, and second elastic strap is adjustable in length.

18. The adjustable back support device of claim 17, wherein all of the first elastic belt, the second elastic belt, first elastic strap, and second elastic strap are adjustable in length.

19. The adjustable back support device of claim 17, wherein at least one of the first elastic belt, the second elastic belt, first elastic strap, and second elastic strap is constructed from a material enabling adjustment of a length thereof.

20. The adjustable back support device of claim 18, wherein all of the first elastic belt, the second elastic belt, first elastic strap, and second elastic strap are constructed from a material enabling adjustment of lengths thereof.

* * * * *